United States Patent [19]

Barabas

[11] Patent Number: 4,704,436

[45] Date of Patent: Nov. 3, 1987

[54] WATER SOLUBLE COMPLEX OF A POLY(VINYLPYRROLIDONE) COPOLYMER AND α-METHYL-(2-METHYLPROPYL)BENZENE ACETIC ACID

[76] Inventor: Eugene S. Barabas, 41 Stanie Brae Dr., Watchung, N.J. 07060

[21] Appl. No.: 858,977

[22] Filed: May 2, 1986

[51] Int. Cl.$^4$ .................. C08F 8/00; C08F 226/10
[52] U.S. Cl. .................. 525/326.9; 525/386; 526/264
[58] Field of Search ............ 525/326.9, 386; 528/367, 486; 526/264

[56] References Cited

FOREIGN PATENT DOCUMENTS 0027613  4/1981  European Pat. Off. .

Primary Examiner—Theodore E. Pertilla

[57] ABSTRACT

The invention relates to a novel water soluble α-methyl-(2-methylpropyl)benzene acetic acid in a complexed state which is derived from the reaction between an N-vinyl-2-pyrrolidone copolymer and the α-methyl-(2-methyl-propyl)benzene acetic acid and to the process for the preparation of said complex.

11 Claims, No Drawings

WATER SOLUBLE COMPLEX OF A POLY(VINYLPYRROLIDONE) COPOLYMER AND α-METHYL-(2-METHYLPROPYL)BENZENE ACETIC ACID

α-Methyl-(2-methylpropyl)benzene acetic acid is a well known anti-inflammatory agent having analgesic and antipyretic properties. It is widely used to control the pain of arthritis and is marketed under the name of Ibuprofen. However, administration of this compound in solution is complicated by its extreme water-insolubility. Because of its application in pharmaceutical areas, it is important that no solvent having toxic or other deleterious side effects be employed for its medicinal use.

Accordingly, it is an object of the present invention to provide α-methy-(2-methylpropyl)benzene acetic acid in a highly water soluble form having no objectionable side effects.

Another object of this invention is to provide a commercially feasible process for the production of α-methyl-2-methylpropyl)benzene acetic acid in highly water soluble form.

These and other objects of the invention will become apparent from the following description and disclosure.

According to this invention there is provided a complexed water soluble product derived from the reaction between a N-vinyl-2-pyrrolidone copolymer and α-methyl-(2-methylpropyl)benzene acetic acid (referred to herein as Ibuprofen). This product is a true complex containing repeating units of the structure which may be formed through hydrogen bonding as shown below.

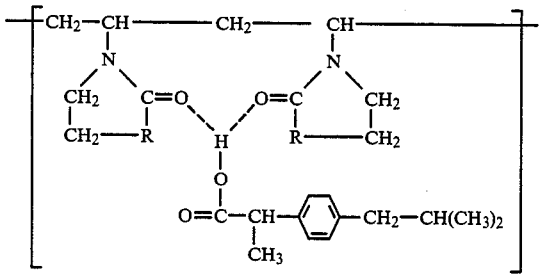

wherein R is —CH$_2$— or —C$_2$H$_4$—. It is to be understood, however, that the above formula represents only one of the possible hydrogen bonded structures that can form in the course of the reaction. It is also probable that complexation takes place, not only by hydrogen bonding but also by hydrophobic bonding and/or by Van der Waals forces to a major or minor extent.

The scope of this invention is not to be restricted by theoretical considerations with respect to the nature of the complex bonding since it will be recognized that the ability of the compound to be complexed and solubilized by poly(vinyl pyrrolidone) depends to a great extent upon the chemical, physical and morphological characteristics of the compound, the hydrophilic-hydrophobic ratio of its structural elements, the nature and relative position of its substituents, the bulkiness of the molecule in general and the substituents in particular. Small differences in any of the above factors may significantly alter the solubilizing capability. While the complexability of the compound with poly(vinylpyrrolidone) may be predicted to some extent, on the chemical character of its substituents, its solubility cannot be predicted on structural similarities alone. Instead a combination of aforesaid factors interacting in the compound to be complexed must be considered. Thus, each compound must be viewed and tested individually for a determination of its solubility.

The complexed product of this invention may also contain a minor amount of non-complexed lactam sites. One factor affecting the number of non-complexed sites is the amount of vinylpyrrolidone contained in the copolymer. Accordingly, for the purposes of this invention, the amount of vinylpyrrolidone in the polymer should be between about 50% and about 95% by weight, between about 70% and about 85% by weight being preferred. The number average molecular weight of the copolymer should be greater than 1,000 and preferably between 10,000 and 500,000. Such copolymers are capable of complexing the water insoluble Ibuprofen to a high degree such that about 8%, up to 30% of the pyrrolidone complexing sites are reacted with the Ibuprofen through complex bonding.

The vinylpyrrolidone copolymer of this invention contains N-vinyl-2-pyrrolidone monomer and a comonomer selected from the group of a di lower alkylamino lower alkyl -acrylate or -methacrylate, e.g. dimethylaminoethylacrylate or -methacrylate, a di lower alkylamino lower alkyl styrene, e.g. dimethylaminomethyl styrene or N-vinyl imidazole. The above copolymers can be unquaternized or quaternized as in the case of GAFQUAT-734 (the 50% quaternized copolymer of 80% N-vinyl-2-pyrrolidone and 20% dimethylaminoethyl methacrylate in alcohol solution).

The complexed units in the polymer may occur in block, random or alternating distribution. In any case, the resulting product contains at least 5% complexed units, preferably at least 9% complexed units, in the product, so as to retain properties associated with the Ibuprofen compound.

Most preferably, the Ibuprofen complexed with the copolymer is present in an amount between about 8 to about 15 weight %. Ibuprofen complexed in this manner exhibits at least a 50 fold increase in water solubility over the uncomplexed compound.

The complexed state of Ibuprofen has been established by experiment showing that at gradual dilution of from 2% to 0.01% in water, no free Ibuprofen separated from the aqueous solution. If the drug were not complexed, it would precipitate from the aqueous solution at a concentration within this range. That the material remains in solution at relatively high dilution, significantly above the solubility limit of uncomplexed Ibuprofen (less than 1 mg in 1 ml H$_2$O at room temperature), is indeed unexpected.

While the complexes of the invention are stable under normal conditions, they are subject to in vivo hydrolytic forces and other physical chemical effects which lead to slow dissociation. Therefore these complexes can function as slow release systems suitable for the sustained delivery of the drug portion of the complex in medical and veterinarial applications.

The Ibuprofen complex of this invention is prepared by a relatively simple and direct process which involves separately dissolving the Ibuprofen and the N-vinylpyrrolidone copolymer in a C$_1$-C$_5$ alcohol, preferably ethanol, to provide solutions having between about 5 and about 25 weight % concentration of the respective reactants. Generally solutions of from about 8% to about 15% by weight of reactive components are preferred. The solutions are then combined in a weight ratio of copolymer to acid of between about 1:1 and about 10:1, preferably in a ratio of 4-7:1, and thoroughly mixed under atmospheric pressure, about 14 psig., or superatmospheric pressure up to 50 psig, at a temperature above 3° C. and below the boiling point of the alcohol solvent, which includes a range of between about 4° C. and about 100° C., preferably between about 10° C. and about 40° C. The mixture is agitated under these conditions for a period of from about 5 minutes to about 3 hours, more often between about 10 and about 30 minutes, to effect the complexing reaction.

After completion of the reaction, the resulting mixture comprising a liquid alcohol phase and a solid product phase is treated to remove solvent by any conventional means, such as rotary evaporation or freeze drying. Rotary evaporation is conducted in vacuo, e.g. under a pressure of from about 2 to about 40 mm Hg, preferably not more than 25 mm Hg. The remaining solids are recovered and dried at a temperature between about 45° C. and about 100° C., preferably between about 50° C. and about 65° C. in vacuo for a period of 1 to 24 hours.

The dried product of the process is readily dissolved in water and the water solubility of the Ibuprofen in this complexed form is increased from 0.01% to at least 5% at room temperature.

Having thus generally described the present invention, reference is now had to the following examples which illustrate preferred embodiments but which are not to be construed as limiting to the scope of the invention as more broadly set forth hereinabove and in the appended claims.

EXAMPLE 1

Alpha-methyl-(2-methylpropyl)benzene acetic acid (10 grams) was dissolved in 90 grams of ethanol and poured into a dropping funnel. GAFQUAT-734 (60 grams) was dissolved in 540 grams of ethanol and poured into a separate dropping funnel. The two solutions were gradually mixed over a period of 15 minutes at room temperature and atmospheric pressure with good agitation in a 2000 milliliter flask. The mixture was stirred for an additional 10 minutes and the flask was then transferred to a rotary evaporator under about 20 mm Hg pressure to remove the ethanol solvent. After evaporation the remaining solid was dried in vacuo at 60° C. overnight.

8 grams of the solid were transferred to a screwcap jar where it was mixed with 20 grams of distilled water on a horizontal shaker for 6 hours at room temperature. After this period the solvent was completely dissolved and the solubility of the alpha-methyl-(2-methylpropyl)benzene acetic acid in water was found to be 5.4%.

As a control, 1 gram of alpha-methyl-(2-methylpropyl)benzene acetic acid was placed in a screwcap jar with 99 grams of distilled water and agitated on a horizontal shaker for 24 hours at room temperature. The solubility of the uncomplexed alpha-methyl-(2-methylpropyl)benzene acetic acid was found to be less than 1 mg in 1 milliliter of water.

EXAMPLE 2

Example 1 was repeated, except that poly(N-vinyl-2-pyrrolidone) was substituted for GAFQUAT-734 and the polymer-alpha-methyl-(2-methylpropyl)benzene acetic acid ratio was 5:1. The resulting complexed compound was found to be wholly insoluble in water.

Example 1 is intended to set forth preferred embodiments of the present invention; however, many variations and modifications in the complexed products will become apparent from the foregoing description and disclosure. For example, other alcohol solvents can be employed as well as the other above mentioned poly(N-vinylpyrrolidone) copolymers to provide complexes wherein the Ibuprofen shows markedly increased water solubility.

What is claimed is:

1. Water soluble α-methyl-(2-methylpropyl) benzene acetic acid in a complexed state derived from the reaction between α-methyl-(2-methylpropyl)-benzene acetic acid and a copolymer of at least 50 weight % of N-vinyl-2-pyrrolidone monomer and a comonomer selected from the group consisting of di lower alkylamino lower alkyl acrylates, di lower alkyl amino lower alkyl methacrylates, di lower alkylamino lower alkyl styrenes and N-vinyl imidazole.

2. The water soluble α-methyl-(2-methylpropyl)benzene acetic acid of claim 1 wherein said copolymer is the copolymer of N-vinyl-2-pyrrolidone and dimethylaminoethyl methacrylate.

3. The complexed product of claim 2 wherein the complexed product contains between about 8 and about 30 weight % of α-methyl-(2-methylpropyl)benzene acetic acid.

4. The complexed product of claim 3 wherein the complexed product contains between about 8 and about 15 weight % of α-methyl-(2-methylpropyl)benzene acetic acid.

5. The product of claim 3 wherein the copolymer comprises about 80% of N-vinyl-2-pyrrolidone monomer.

6. The complexed product of claim 2 containing repeating units of α-methyl-(2-methylpropyl) benzene acetic acid/N-vinyl-2-pyrrolidone complexed moieties.

7. The process for producing the complexed compound of claim 1 which comprises: mixing alcoholic solutions of α-methyl-(2-methylpropyl) benzene acetic acid and a copolymer of N-vinyl-2-pyrrolidone containing not more than 50% of a comonomer selected from the group consisting of a di- lower alkylamino lower alkyl acrylate, a di- lower alkylamino lower alkyl methacrylate, a di- lower alkylamino lower alkyl styrene and N-vinyl imidazole and having a number average molecular weight above 1,000 in a mole ratio of copolymer to α-methyl-(2-methylpropyl) benzene acetic acid of between about 1:1 and about 10:1, agitating the mixture under a pressure of from about atmospheric to about 50 psig at a temperature of from about 4° C. to about 100° C. and below the boiling point of said alcohol, for a period of from about 5 minutes to about 3 hours, to form a liquid solvent phase and a solid complexed product phase, separating said solvent from said complexed product, drying said complexed product and recovering the dried solid as the complexed product of the reaction.

8. The process of claim 7 wherein a $C_1$ to $C_5$ alcohol forms the alcoholic solutions of the reactants and the reactants are present in said solutions in a concentration of between about 5% and about 25% by weight.

9. The process of claim 7 wherein said copolymer is poly(N-vinyl-2-pyrrolidone/dimethylamino ethyl methacrylate) and wherein the N-vinyl-2-pyrrolidone comprises 80% of the copolymer.

10. The process of claim 9 wherein the poly(N-vinyl-2-pyrrolidone) solution is mixed with the α-methyl-(2 methylpropyl) benzene acidic acid solution in a weight ratio of between about 4:1 and about 7:1 and wherein the mixture is heated to a temperature of from about 10° C. to about 40° C. under a pressure of from about 14 to about 50 psig.

11. The process of claim 10 wherein the complexing reaction is effected at atmospheric pressure.

* * * * *